US010634610B2

United States Patent
Adjali et al.

(10) Patent No.: US 10,634,610 B2
(45) Date of Patent: Apr. 28, 2020

(54) METHOD FOR ON-LINE DETERMINATION OF A BASICITY INDEX OF A LIQUID BODY AND USE OF SAID METHOD FOR A LUBRICANT

(71) Applicant: AVENISENSE, Le Bourget-du-lac (FR)

(72) Inventors: Mustapha Adjali, Aix les Bains (FR); Raphael Juston, Chambery (FR); François Chaudoreille, Gresy sur Aix (FR)

(73) Assignee: WIKA TECH S.A.S., Le Bourget-du-Lac (FR)

( * ) Notice: Subject to any disclaimer, the term of this patent is extended or adjusted under 35 U.S.C. 154(b) by 146 days.

(21) Appl. No.: 15/748,370

(22) PCT Filed: Jul. 26, 2016

(86) PCT No.: PCT/EP2016/067743
§ 371 (c)(1),
(2) Date: Jan. 29, 2018

(87) PCT Pub. No.: WO2017/017082
PCT Pub. Date: Feb. 2, 2017

(65) Prior Publication Data
US 2018/0217058 A1  Aug. 2, 2018

(30) Foreign Application Priority Data

Jul. 27, 2015  (FR) .................................... 15 57138

(51) Int. Cl.
*G01N 21/3577* (2014.01)
*G01N 33/28* (2006.01)

(52) U.S. Cl.
CPC ..... *G01N 21/3577* (2013.01); *G01N 33/2888* (2013.01); *G01N 33/2876* (2013.01); *G01N 2201/129* (2013.01)

(58) Field of Classification Search
CPC .. G01N 21/59; G01N 21/314; G01N 2201/12; G01N 21/51; G01N 21/255;
(Continued)

(56) References Cited

U.S. PATENT DOCUMENTS

| 7,741,122 B2* | 6/2010 | Reischman | .......... G01N 33/287 436/119 |
| 2003/0164451 A1* | 9/2003 | Reischman | ........ G01N 33/2876 250/339.12 |
| 2007/0084271 A1* | 4/2007 | Boyle | ................ G01N 33/2876 73/53.05 |

FOREIGN PATENT DOCUMENTS

| CN | 101782512 B | 7/2012 |
| DE | 19650397 A1 | 6/1998 |

(Continued)

OTHER PUBLICATIONS

Al-Ghouti et al., "Application of Chemometrics and FTIR for Determination of Viscosity Index and Base Number of Motor Oils", Talanta, 2010, pp. 1096-1101, vol. 81.

(Continued)

*Primary Examiner* — Brandi N Hopkins
(74) *Attorney, Agent, or Firm* — Thompson Coburn LLP; Steven M. Ritchey (57) ABSTRACT

A method for determining a basicity index of a liquid body comprising: (a) detecting an intensity of an infrared signal passing through a sample of the liquid body; (b) calculating a transmittance value of infrared waves through the sample for p wave numbers, wherein p in a natural integer greater than or equal to two; and (c) determining the basicity index of the liquid body, BN, wherein of $BN = Tr \cdot M_{(p \times 1)} + R$, Tr is a set of transmittance values calculated in step b, $M_{(p \times 1)}$ is a set of data of a model, the set of data containing coefficients determined from measured basicity index values and measured transmittance values of reference liquid bodies, (Continued)

and R is a residue of the model, determined from the measured basicity index values and the measured transmittance values of the reference liquid bodies.

17 Claims, 5 Drawing Sheets

(58) Field of Classification Search
CPC .... G01N 21/95; G01N 21/5907; G01N 25/08; G01N 33/2876; G01N 35/00871; G01N 33/287; Y10T 436/18
See application file for complete search history.

(56) References Cited

FOREIGN PATENT DOCUMENTS

| | | |
|---|---|---|
| WO | 03/073075 A2 | 9/2003 |
| WO | 2013/186338 A1 | 12/2013 |

OTHER PUBLICATIONS

French Search Report for FR 1557138 dated Jun. 20, 2016.
International Search Report and Written Opinion for PCT/EP2016/067743 dated Oct. 18, 2016.
Mohammadi et al., "A Low Cost Mid-Infrared Sensor for On Line Contamination of Monitoring of Lubricating Oils in Marine Engines", Proceedings of SPIE, 2010, 77260M, 12 pages, vol. 7726.
Winterfield et al., "Automated Acid and Base Number Determination of Mineral-Based Lubricants by Fourier Transform Infrared Spectroscopy: Commercial Laboratory Evaluation", Journal of Laboratory Automation, 2014, pp. 577-586, vol. 19, No. 6.

\* cited by examiner

METHOD FOR ON-LINE DETERMINATION OF A BASICITY INDEX OF A LIQUID BODY AND USE OF SAID METHOD FOR A LUBRICANT

CROSS-REFERENCE TO RELATED APPLICATIONS

This application is a U.S. National Phase application of PCT/EP2016/067743, filed on Jul. 26, 2016, claiming the benefit of French Application No. 1557138, filed on Jul. 27, 2015, each of which is incorporated herein by reference in its entirety.

FIELD OF THE INVENTION

The present invention relates to a method for on-line determination of a basicity index of a liquid body, in particular a lubricant. The present invention is in particular applicable to the determination of the basicity of a lubricant circulating in a piece of equipment, such as a ship's engine.

BACKGROUND OF THE INVENTION

In the field of internal combustion engines used on merchant ships, it is known that the situation of an engine must be monitored by analyzing a lubricant circulating in this engine. Such an analysis makes it possible to detect wear or corrosion phenomena that tend to occur in an engine. In the past, the operation of the engines was relatively stabilized, and it was sufficient to inspect the quality of a lubricant periodically, at ports of call, to anticipate the maintenance operations to be performed. Today, engines are increasingly elaborate and sensitive to wear or corrosion phenomena, such that analyses must be done at sea, in particular to monitor the base number (BN) of the engine oil. This requires training staff and carrying a elaborate equipment on board, the operation of which is relatively difficult to master, even by a trained sailor. Furthermore, this increases the crew's workload.

In this context, it is known from the article "*A low cost mid-infrared sensor for on line contamination monitoring of lubricating oils in marine engines*" by Ben Mohammadi et al. (Optical Sensing and Detection Conference—Brussels—4/12-15/2010) to provide a system for analyzing the TBN (Total Base Number), using a sensor in which a sample of the lubricant to be studied is placed. The equipment used is elaborate, and complex to manipulate, to the point that it may be difficult to place on board a ship. Furthermore, this approach requires the user to be very knowledgeable about the measured phenomena, to the point that it is not necessarily within grasp for an ordinary seaman. This equipment uses a model that is only suitable for a single type of oil. It therefore becomes very difficult to incorporate it into a process where the liquids used change continuously.

WO-A-03/073075 discloses a method for analyzing the base number of a lubricant during which a measurement, done on a sample of the lubricant to be inspected, is compared to measurements done on reference samples. The method considered in this document is based on the use of the absorbance of the lubricant, which is relatively imprecise, since it is sensitive to noise from the collected information. Indeed, the erratic or "noise" values risk being considered as relevant as the significant values measured. This technique requires a "blank" before each measurement, which is restrictive and leads to lost time. Furthermore, it is necessary to clean the sensor after each measurement, since residue from the previous sample would alter the current measurement. Lastly, the model obtained with this method is valid for a threshold lubricant type and is highly dependent on the reading precision of the absorbance.

It is also known from WO-A-2013/186338 to determine an overall basicity index of a lubricant through FTIR analysis of an absorption spectrum. This method is complex to implement.

In general, comparable problems arise when the basicity index of a liquid body must be determined.

BRIEF SUMMARY OF THE INVENTION

The invention more particularly aims to resolve these drawbacks by proposing a new method for determining a basicity index of a liquid body that is reliable and less dependent on noise in the collected data, while being easy for an operator to carry out.

To that end, the invention relates to a method for the on-line determination of a basicity index of a liquid body to be characterized, in particular a lubricant, by mid-infrared spectroscopy, in which at least one step a is carried out consisting of detecting the intensity of an infrared signal passing through a sample of the liquid body to be characterized. According to the invention, this method also comprises at least the additional steps consisting of:

b) subsequent to step a, calculating the transmittance value of infrared waves through the sample for p wave numbers, where p is a natural integer greater than or equal to two;

c) expressing the basicity index of the liquid body to be characterized in the form $$BN = Tr \cdot M_{(p \times 1)} + R$$

where BN is the basicity index of the lubricant to be characterized,

Tr is a set of transmittance values calculated in step b $M_{(p \times 1)}$ is a set of model data containing the coefficients determined from the measured values of the basicity index and from the measured transmittance values for the reference liquid bodies, R is a residue of the model, determined from the measured basicity and transmittance values.

Owing to the invention, the basicity index can automatically be calculated in step c based on the transmittance values detected in step b and the previously established model, without the user having to consult data tables that are difficult to read and may lead him into interpretation errors. In particular, steps b and c may be automated, which makes it possible to consider implementing the inventive method on board a ship, under the oversight of an ordinary seaman alone. The invention may also be carried out to determine the basicity index of another liquid used under other circumstances.

According to advantageous but optional aspects of the invention, such a method may incorporate one or more of the following features, considered in any technically allowable combination:

During step b), the transmittance value for each wave number is calculated as the ratio of the intensity of the infrared signal passing through the sample to the intensity of the signal when empty.

Alternatively, step b) comprises elementary steps b1) and b2) consisting, for b1), of calculating, for each wave number, the ratio of the intensity of the infrared signal passing through the sample to the intensity of the signal when empty, and for b2), of calculating the transmittance value in the form of a corrected value of the ratio calculated in step b1). In this case, it is possible to provide that, during elementary step b2), the value of the ratio is corrected by filtering and/or removal of a baseline.

The transmittance value comprises a unidirectional matrix with one row and p columns and the set of model data is a unidirectional matrix with p rows and one column.

The method comprises prior steps, carried out to determine the model and consisting of:
α1) detecting the intensity $I_0(N)$ of an infrared signal, for the p wave numbers, when empty,
α2) detecting the intensity $I(N)$ of an infrared signal, for the p wave numbers, within n samples, each representative of a reference liquid body;
α3) calculating the transmittance of each reference liquid body as a set of values defined, for each wave number, as the ratio of the intensity detected in step α2 to the intensity detected in step α1;
α4) creating a first set of reference data comprising the transmittance values calculated in step α3 for the n samples and for the p wave numbers;
α5) measuring the basicity index of each reference liquid body;
α6) creating a second set of reference data comprising the n basicity index values measured in step α5; and
α7) determining, by calculation, the set of data and the residue of the model, based on the first and second sets of reference data.

During step α3), the transmittance of each reference liquid body is calculated as a set of values defined, for each wave number, as the ratio of the intensity detected in step α2) to the intensity detected in step α1).

Alternatively, step α3) comprises elementary steps α31) and α32) consisting, for α31), of calculating, for each wave number, the ratio of the intensity detected in step α2) to the intensity detected in step α1), and for α32), of calculating the transmittance value in the form of a corrected value of the ratio calculated in step α31), preferably by filtering and/or removing a baseline.

The first set of reference data is a two-dimensional matrix with n rows and p columns, each row comprising transmittance values calculated in step α3 for a reference liquid body and p wave numbers and each column comprising transmittance values calculated for a wave number and the n reference liquid bodies, while the second set of reference data is a unidirectional matrix with n rows and one column.

The method comprises additional prior steps, carried out during step α7 to determine the model and consisting of:
β1) defining a first set of calculation data that is an image of the first set of reference data;
β2) defining a second set of calculation data that is an image of the second set of reference data;
β3) defining a first variable dependent on the first set of calculation data according to the relationship: T=X·W
where T is the first variable,
X is the first set of calculation data,
W is a first weight coefficient,
β4) defining a second variable dependent on the second set of calculation data according to the relationship: C=Y·U
where C is the second variable,
Y is the second set of calculation data,
U is a second weight coefficient, and
β5) calculating the values of the two weight coefficients iteratively, while maximizing the covariance of the first and second variables.

The method comprises additional prior steps, carried out during step α7 to determine the model and consisting of:
β6) applying, to each iteration, a linear regression of the first set of calculation data on the first variable;
β7) applying, to each iteration, a linear regression of the second set of calculation data on the first variable;
β8) calculating, in each iteration, an estimated value of the first set of calculation data, by applying a transpose of a slope of the linear regression, determined in that step, to the first calculated variable in that step.
β9) calculating, in each iteration, an actual value of the first set of calculation data, by subtracting the estimated value calculated in step β8 from an actual value of this first set of calculation data calculated in the previous iteration.
β10) calculating, in each iteration of step β5, an estimated value of the second set of calculation data, by applying a transpose of a slope of the linear regression, determined in that iteration, to the first calculated variable in that iteration.
β11) calculating, in each iteration, an actual value of the second set of calculation data, by subtracting the estimated value calculated in step β10 from an actual value of this second set of calculation data calculated in the previous iteration.

Steps β5 to β11 are repeated until the value of the second set of data becomes lower than a predetermined threshold value.

The first variable is a two-dimensional matrix with n rows and p columns, the second variable is a unidirectional matrix with n rows and one column, the first weight coefficient is a two-dimensional matrix with p rows and p columns, the second weight coefficient is a number, whereas, in each iteration, the weight coefficients are calculated according to the equations:

$$W_k = {}^tX_{k-1}Y_{k-1}{}^tY_{k-1}X_{k-1}$$

$$U_k = {}^tY_{k-1}X_{k-1}{}^tX_{k-1}Y_{k-1}$$

where the index k applied to a matrix indicates the value of that matrix in iteration k, that the linear regression of step β6 is done based on an equation of type:

$$X_{k-1} = T_k{}^tp_k + X_{k_k}$$

where $p_k$ is a matrix of regression coefficients determined using the method of least squares and expressed in the form:

$$p_k = \frac{{}^tX_{k-1}T_k}{{}^tT_kT_k}$$

the linear regression of step β7 is done based on an equation of the type:

$$Y_{k-1} = T_k{}^tq_k + Y_{k_k}$$

where $q_k$ is a matrix of regression coefficients determined by the method of least squares and that is expressed in the form:

$$q_k = \frac{{}^tY_{k-1}T_k}{{}^tT_kT_k}$$

The method comprises additional prior steps γ1 and γ2, carried out to determine the model and consisting of expressing the second set of reference data as a function of the first variable according to the relationship:

$$Y^0 = \sum_1^K W_k{}^t q_k + Y_k$$

where K is the number of iterations of step β5), k is a natural number between 1 and K, Tk is the first variable with iteration rank k, $^t q_k$ is the transpose of the linear regression slope used in step β10)

$Y_K$ is the second set of calculation data with iteration rank K, and determining the set of data of the model and the residue as respectively being equal to $M_{(p \times 1)} = \Sigma_1^K W_k{}^t q_k$ and $R = Y_K$, where $W_k$ is the weight coefficient with iteration rank k.

The invention also relates to the use of a method as mentioned above to determine the basicity index of a lubricant circulating in a piece of equipment of a ship, in particular in a ship engine.

BRIEF DESCRIPTION OF THE DRAWINGS

The invention will be better understood, and other advantages thereof will appear more clearly, in light of the following description of two embodiments of a method according to its principle, provided solely as an example and done in reference to the appended drawings, in which.

DETAILED DESCRIPTION OF THE INVENTION

Figure 1:
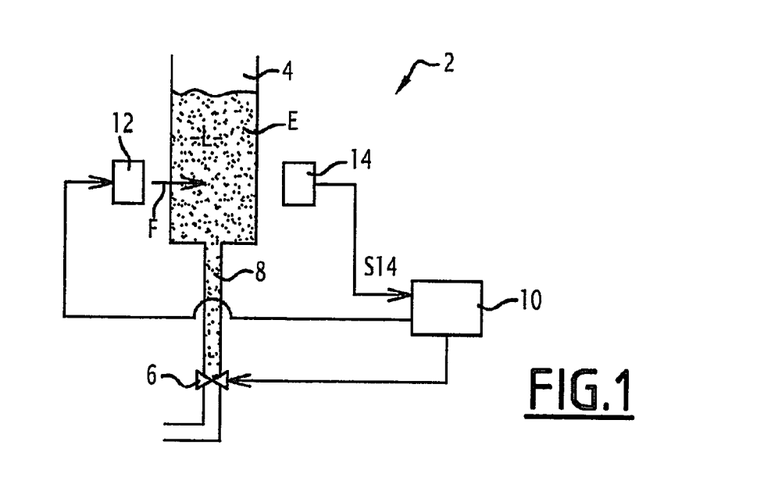
FIG. 1 is a schematic block illustration of a facility making it possible to carry out the inventive method.

The facility 2 shown in FIG. 1 comprises a reservoir 4 in which a sample E of a lubricant L for a ship propulsion engine is stored and which forms an analysis chamber, the inner volume of which can be relatively small, in particular smaller than 1 cm$^3$. In practice, the inner volume of the reservoir 4 can be smaller than 0.1 cm$^3$. The reservoir 4 is supplied with a quantity of lubricant intended to make up the sample E, either by pouring a quantity of lubricant L intended to make up the sample by hand, or from a tapping connected on a lubricant discharge pipe, at the outlet of the ship's engine. A valve 6 mounted on a bleed pipe 8 of the reservoir 4 makes it possible to monitor the evacuation of the quantity of lubricant present in the reservoir 4. The valve 6 is a solenoid valve commanded by an electronic unit 10 configured for that purpose.

The facility 2 also comprises a transmitter 12 and a receiver 14 also controlled by the electronic control unit 10. In particular, the receiver 14 is capable of delivering, to the electronic control unit 10, an electrical signal S14 representative of an infrared signal that it detects.

The transmitter 12 and the receiver 14 are configured to work together in the mid-infrared range. The transmitter 12 sends waves in the mid-infrared range, i.e., with a number of waves N comprised between 4000 cm$^{-1}$ and 600 cm$^{-1}$. The sensor 14 is in fact a spectroscope that can work over the aforementioned range of wave numbers. In practice, to determine the basicity index of a ship engine lubricant, the transmitter 12 and the receiver 14 work in a range of wave numbers N comprised between about 1900 cm$^{-1}$ and about 900 cm$^{-1}$. This is due to the fact that the response to the infrared rays of various tracers of the basicity index, in particular calcium or magnesium carbonate, sulfonates, is in this range.

When a sample E of lubricant is present in the reservoir 4, it is possible to send, with the transmitter 12, a signal in the form of a beam F of infrared light that is detected by the receiver 14 after having traversed the walls of the container 4 and the lubricant sample E. The method according to the present invention is based on the determination of the transmittance of a sample E of lubricant L placed in the reservoir 4, this transmittance being used to determine the basicity index BN of this lubricant.

The transmittance Tr of a liquid is defined as the ratio $I/I_0$, where I is the intensity of the beam F detected by the receiver 14 when this beam F traverses both the reservoir 4 and the sample E of this liquid, and $I_0$ is the same intensity when the beam F with the reservoir 4 is empty of sample, therefore containing air, or with the reservoir removed. In this case where the reservoir does not contain any sample or has been removed, this is called an "empty" measurement, since there is no sample in the facility 2. In practice, the transmittance $T_r$ is measured for a liquid with different values of the wave number N of the beam F, over the range 1900 cm$^{-1}$ 900 cm$^{-1}$ cited above.

Calculation of the Basicity Index

At the beginning of use of the facility 2, a prior step z is carried out during which the intensity $I_0(N)$ of the beam F captured by the receiver 14 is determined for different wave numbers N, when the reservoir 4 is removed or emptied of any sample. In this example, this determination takes place for 128 wave numbers N. One thus creates a set of 128 empty intensity values $I_0(N)$ for the different values of wave numbers N. This is shown by step z in FIG. 2.

Figure 2:
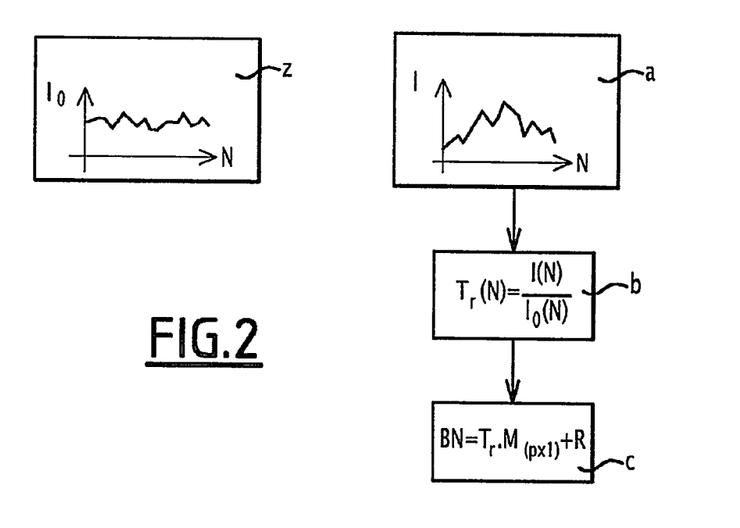
FIG. 2 is a block diagram of a first method according to the invention.

This step z is carried out a single time, even if several samples E are next studied using the steps described below. Thus, it is not necessary to have a "blank" with the facility 2 before each measurement.

The number p of wave numbers N for which the measurement is done can be chosen to be different from 128, for example equal to 64 or 256, based on the desired precision. This number is greater than or equal to 2.

When the basicity index of the lubricant L must be determined on-line, a quantity of this lubricant is introduced into the reservoir 4 to make up the sample E, within the measuring line shown in FIG. 1 as shown in FIG. 1 [sic], and the intensity I(N) of the beam F detected by the receiver 14 is measured, when this beam F has traversed both the reservoir 4 and the sample E of lubricant L for each of the p wave numbers. This is done during a first step a of the inventive method.

One then calculates, for each number of waves N, the value of the transmittance Tr(N) as being equal to the ratio $I(N)/I_0(N)$ for this number of waves. This takes place during a step b and makes it possible to build the transmittance spectrum Tr of the sample measured with the facility 2, in the form of a matrix with one row and p columns that can be written as follows:

$$Tr_{(1 \times p)} = [tr_1 tr_2 \ldots tr_p] \quad \text{(equation 1)}$$

where p is the number of waves taken into account, this number being greater than or equal to 2, as explained above, and for example equal to 128.

When this transmittance matrix Tr is known, one uses, in a subsequent step c of the inventive method, a model calculated in the laboratory and that comprises a unidirectional matrix $M_{(p\times1)}$ with p rows and one column. This matrix $M_{(p\times1)}$ is in turn made up of weight $m_i$ values for the p wave numbers, where i is a natural integer between 1 and p. It is expressed according to the following relationship:

$$M_{(p\times 1)} = \begin{bmatrix} m_1 \\ \vdots \\ m_p \end{bmatrix} \quad \text{(equation 2)}$$

The method for calculating these weight values $m_i$ is described below, in the "calculation of the model" section.

The basicity index of the lubricant L, often called BN (base number), or TBN (total base number), is calculated in this step c by the following matricial relationship:

$$BN = Tr \cdot M_{(p\times 1)} + \quad \text{(equation 3)}$$

where BN is the basicity index,

Tr is the transmittance spectrum of the sample, $M_{(p\times 1)}$ is the matrix of the model, and R is a residue, i.e., an accepted error of the model, which is expressed in the form of a number.

Thus, the method according to the invention, which uses equation 3 to calculate the basicity index BN, can be automated, in particular done in the unit 10, without the user needing any particular skills and having to spend a long period studying hard-to-read reference tables.

In other words, steps b and c mentioned above can be carried out automatically once the lubricant sample E is in place in the reservoir 4, which makes it possible to calculate the basicity index quickly and reliably and to display a value directly readable by the user, or even to send this value automatically to a control member of the engine from which the lubricant L is taken. In other words, all of the calculation steps are integrated and the sensor only returns the final value of the basicity index via a specific industrial communication protocol. No outside intervention or manipulation is necessary.

In the aforementioned step a), the valve 6 is closed and the intensity I(N) of the beam F is measured while the liquid is at rest in the reservoir 4. Alternatively, this measurement may take place "in passing", i.e., when the liquid flows in the reservoir 4, which then acts as a pipe segment, while the valve 6 is open.

Calculation of the Model

The calculation of the model takes place during the performance of steps a to c mentioned above and seeks to determine the matrix $M_{(p\times 1)}$ and the residue R. Once this model is calculated, it can be used to determine the basicity index of several samples, using steps a to c, as explained above.

To calculate the model, one proceeds from n lubricant samples whose basicity index can be measured using a known technique, n being an integer greater than or equal to 2.

First, transmittance spectrums of these n samples are acquired using the transmitter 12 and the sensor or receiver 14. To that end, a first step α1 is carried out during which the intensity of the signal formed by the beam F is detected empty, when the reservoir 4 is removed or is present but does not contain any sample. This step α1 is the same as step z mentioned above regarding the definition of the transmittance. In practice, step α1 can be carried out during the calculation of the model, and its result can be used during step b mentioned above. Step z mentioned above is therefore optional.

A second step α2 is also carried out, during which the intensity of the signal formed by the beam F is detected through each of the n samples and the reservoir 4. This step α2 is of the same type as step α, except that it is done with the n reference samples. After carrying out steps α1 and α2, the unit 10 automatically carries out a step α3 during which the transmittance Tr of each of the n samples is calculated for each of the p considered wave numbers.

Figure 3:
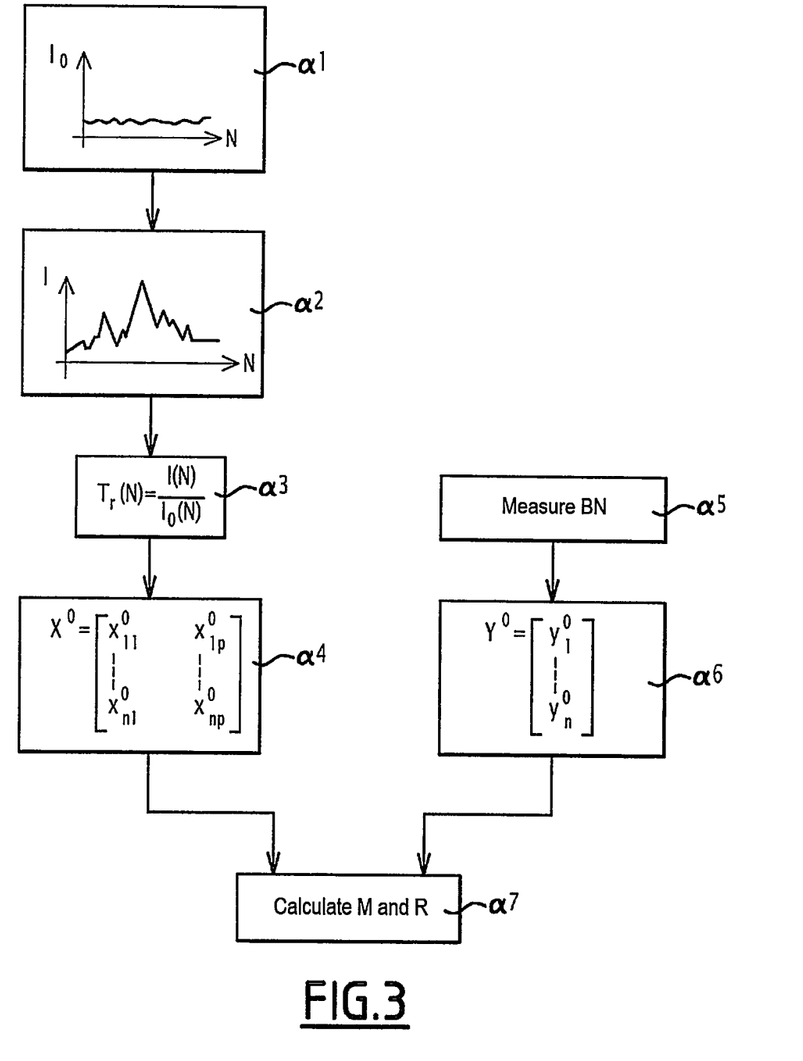
FIG. 3 is a block diagram of certain prior steps, useful to the method of FIG. 2.

This makes it possible to generate, in a following step α4, a first set of reference data $X^0$ that is built in the form of a matrix with n rows and p columns, expressed in the form:

$$X^0_{(n\times p)} = \begin{bmatrix} x^0_{11} & x^0_{12} & \ldots & x^0_{1p} \\ x^0_{21} & x^0_{22} & \ldots & x^0_{2p} \\ \vdots & \vdots & & \vdots \\ x^0_{n1} & x^0_{n2} & \ldots & x^0_{np} \end{bmatrix}, \quad \text{(equation 4)}$$

In this matrix, each row gives the transmittance values of a sample for the p wave numbers and each column gives the transmittance values of the n samples for a wave number.

Secondly, during a step α5, a laboratory analysis is done for these n samples. The basicity index of each of the samples is measured using the ASTM D2896 method.

Alternatively, another method for measuring the basicity index can be implemented, for example potentiometric titration, or ASTM D5984 or ASTM D974 colorimetric indicator titration.

This measurement in step α5 makes it possible to generate, in a following step α6, a second set of reference data $Y^0$ that is built in the form of a unidirectional matrix with n rows and 1 column and that is expressed in the form:

$$Y^0_{(n\times 1)} = \begin{bmatrix} y^0_1 \\ \vdots \\ y^0_n \end{bmatrix} \quad \text{(equation 5)}$$

Alternatively, steps α5 and α6 are carried out before steps α1 to α4, or at the same time.

From the sets of reference data $X^0$ and $Y^0$, the method calculates, in a step α7, the values of the matrix $M_{(p\times 1)}$ and the residue R. This step α7 is shown in FIG. 3 with steps α1 to α6 and, with these steps, constitutes the preliminary part of the inventive method. Step α7 is shown in detail in FIG. 4.

Figure 4:
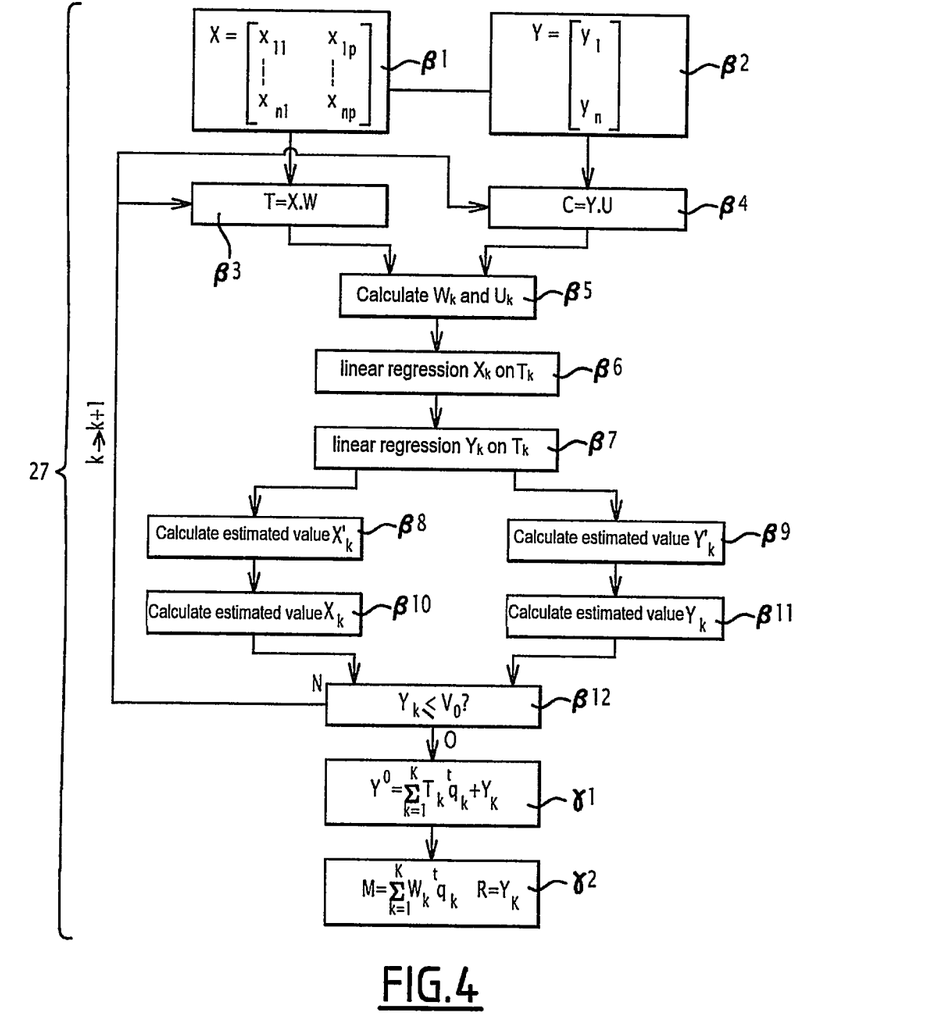
FIG. 4 is a block diagram of certain other prior steps, useful to the method of FIG. 2.

During this step α7 and from the sets $X^0$ and $Y^0$ of reference data, it is possible to build, respectively in two steps β1 and β2, two sets of calculation data, which are respectively images of the sets $X^0$ and $Y^0$, in the form of matricial variables X and Y defined as follows:

$$X_{(n\times p)} = \begin{bmatrix} x_{11} & x_{12} & \ldots & x_{1p} \\ x_{21} & x_{22} & \ldots & x_{2p} \\ \vdots & \vdots & & \vdots \\ x_{n1} & x_{n2} & \ldots & x_{np} \end{bmatrix}, \quad \text{(equation 6)}$$

-continued $$Y_{(n\times 1)} = \begin{bmatrix} y_1 \\ \vdots \\ y_n \end{bmatrix} \quad \text{(equation 7)}$$

where $X_{(n\times p)}$ is a matrix representing n spectrums of transmittance values with p wave numbers and $Y_{(n\times 1)}$ is a matrix representing values of the basicity index BN corresponding to the n samples. X is an input variable and Y is an output variable for equation 3, since Y corresponds to the basicity index or BN values.

It is desirable to be able to use equation 3, by writing the output variable Y corresponding to the basicity index values BN of the n samples, as a function of the input variable X corresponding to the associated transmittance spectrums.

The aim of the calculation is therefore to write:

$$Y = X \cdot B + \varepsilon \quad \text{(equation 8)}$$

where B is a matrix with p rows and one column and $\varepsilon$ is a residue.

In other words, the aim is to find a relationship between these two properties X and Y that is expressed as the relationship of equation 3 that one wishes to use in step c. This makes it possible to consider that the matrix B of equation 8 is equal [to] the matrix M and that the value c is equal to the residue R. The writing of equation 8 therefore seeks to determine the matrix $M_{(p\times 1)}$ of the model and its residue R.

To that end, new variables T and C are created by performing a linear transform of the properties X and Y, respectively during a step β3 and a step β4, in the form:

$$T = X \cdot W \quad \text{(equation 9)}$$

and $$C = Y \cdot U \quad \text{(equation 10)}$$

where W and U are weight coefficients for the variables X and Y.

The transform of the properties X and Y during steps β3 and β4 is done to maximize the covariance between the new created variables T and C with the aim of finding the correlation between the properties X and Y as described in equation 8. The covariance Cov(T,C) of the variables T and C is expressed in the following form:

$$\text{Cov}(T, C) = \text{Cov}(XW, YU) = \frac{1}{n-1}{}^tW^tXYU \quad \text{(equation 11)}$$

In other words, one seeks to calculate the weight coefficients W and U that maximize equation 11.

The resolution of this problem is done using an iterative method, considering successive values $W_k$ and $U_k$ of the weight coefficients, where k is the iteration. It consists of the following steps, which will be repeated K times, K being an integer greater than or equal to 2:

Initially, one has $X = X^0$ and $Y = Y^0$.

In a step β5, one calculates $W_k$ and $U_k$ for k comprised between 1 and K.

According to AgnarHöskuldsson (PLS regression methods. Journal of chemometrics, 2:221-228, 1988), the solutions $W_k$ and $U_k$ of equation 11 have the following form:

$$W_k = {}^tX_{k-1}Y_{k-1}{}^tY_{k-1}X_{k-1} \quad \text{(equation 12)}$$

and $$U_k = {}^tY_{k-1}X_{k-1}{}^tX_{k-1}Y_{k-1} \quad \text{(equation 13)}$$

This makes it possible to calculate $T_k$ and $C_k$ as follows:

$$T_k = X_{k-1}W_k \quad \text{(equation 14)}$$

and $$C_k = Y_{k-1}U_k \quad \text{(equation 15)}$$

One then proceeds, respectively during a step β6 and during a step β7, with a regression of $X_{k-1}$ on $T_k$ and $C_k$, so as to be able to estimate $X_{k-1}$ and $Y_{k-1}$ with the new variables $T_k$ and $C_k$, and more particularly to estimate $X_{k-1}$ and $Y_{k-1}$ as a function of $T_k$ according to the relationships:

$$X_{k-1} = T_k {}^t p_k + X_{k_k} \quad \text{(equation 16)}$$

and $$Y_{k-1} = T_k {}^t q_k + Y_{k_k} \quad \text{(equation 17)}$$

The regression on $C_k$ is not used to calculate the model itself, but to assess its performance.

One therefore calculates, during these steps β6 and β7, regression coefficients $p_k$ and $q_k$ corresponding to the regression of $X_k$ and $Y_k$ respectively on $T_k$, using the method of least squares. These regression coefficients $p_k$ and $q_k$ are matrices with p rows and q columns. One obtains:

$$p_k = \frac{{}^tX_{k-1}T_k}{{}^tT_kT_k} \quad \text{(equation 16)}$$

and $$q_k = \frac{{}^tY_{k-1}T_k}{{}^tT_kT_k} \quad \text{(equation 17)}$$

Alternatively, a regression method other than that of least squares can be used. In particular, it is possible to perform an estimate using the maximum likelihood method or the Bayesian interference method.

During a following step β8, the result of the regression is used to calculate an estimated value $X'_k$ of the property X with iteration rank k, according to the following relationship:

$$X'_k = T_k {}^t p_k \quad \text{(equation 18)}$$

Likewise, during a following step β9, an estimated value $Y'_k$ is calculated of the property Y with iteration rank k, according to the following relationship:

$$Y'_k = T_k {}^t q_k \quad \text{(equation 19)}$$

From equations 18 and 19, one deduces, in two subsequent steps β10 and β11, the actual value $X_k$ and $Y_k$ of the properties X and Y with iteration rank k, using the following equations:

$$X_k = X_{k-1} X'_k = X_{k-1} - T_k {}^t p_k \quad \text{(equation 20)}$$

where $X_{k-1}$ is the actual calculated value with iteration rank k−1 and $X'_k$ or $T_k {}^t p_k$ is the estimated value with iteration rank k, and $$Y_k = Y_{k-1} Y'_k = Y_{k-1} - T_k {}^t q_k \quad \text{(equation 21)}$$

where $Y_{k-1}$ is the actual calculated value with iteration rank k−1 and $Y'_k$ or $T_k {}^t q_k$ is the estimated value with iteration rank k.

This therefore results in writing $X_{k-1}$ and $Y_{k-1}$ as a function of the new variable $T_k$, or:

$$X_{k-1} = T_k {}^t p_k + X_k \quad \text{(equation 22)}$$

and $$Y_{k-1} = T_k {}^t q_k + Y_k \quad \text{(equation 23)}$$

One next increments the value of k, then reiterates steps β5 to β11, using, as initial values for each iteration k+1, the values $X_k$ and $Y_k$, obtained during the previous iteration k through equations 20 and 21.

These calculations steps β5 to β11 are reiterated K times until obtaining a satisfactory correlation between the measured output values of the model $Y_{(n \times 1)}{}^0$ and the input values corresponding to the measurements done $X_{(n \times p)}{}^0$ when these properties are linked by the relationship of equation 8, in the following form:

$$Y_{(n \times 1)}{}^0 = X_{(n \times p)}{}^0 \cdot B + \varepsilon \quad \text{(equation 24)}$$

This satisfactory correlation is considered to be achieved when the residue ε in this equation 24 has a value below a predetermined threshold value $V_0$ as a function of the desired precision for the method for calculating the basicity index. If this is the case, equation 24 is considered to be satisfied and the iteration is stopped in a step β12. Otherwise, the iteration continues, returning to steps β3 and β4. A calculation of the mean quadratic error also makes it possible to determine K and stop the iteration in step β12.

Below, the first two iterations of steps β5 to β12 are explained in detail, as an example.

By defining equations 6 and 7, one has:

$$X_{(n \times p)} = \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix},$$

$$Y_{(n \times 1)} = \begin{bmatrix} y_1 \\ \vdots \\ y_n \end{bmatrix}$$

1 Iteration 1: For k=1 $X = X^0$ and $Y = Y^0$ 1.1 Calculation of $T_1$ in Step β3 and $C_1$ in Step β4

$$T_1 = X^0 W_1 = \begin{bmatrix} x_{11}^0 & x_{12}^0 & \cdots & x_{1p}^0 \\ x_{21}^0 & x_{22}^0 & \cdots & x_{2p}^0 \\ \vdots & \vdots & & \vdots \\ x_{n1}^0 & x_{n2}^0 & \cdots & x_{np}^0 \end{bmatrix} \begin{bmatrix} w_{11} & w_{12} & \cdots & w_{1p} \\ w_{21} & w_{22} & \cdots & w_{2p} \\ \vdots & \vdots & & \vdots \\ w_{p1} & w_{p2} & \cdots & w_{pp} \end{bmatrix}$$

$$T_1 = \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix}$$

$$C_1 = Y^0 U_1 = \begin{bmatrix} y_1^0 \\ \vdots \\ y_n^0 \end{bmatrix} [U_1] = \begin{bmatrix} c_1 \\ \vdots \\ c_n \end{bmatrix}$$

1.2 Calculation of $W_1$ and $U_1$ in Step β5

$$W_1 = {}^t X_0 {}^t Y_0 Y_0 X_0$$

$$W_1 = \begin{bmatrix} x_{11}^0 & x_{21}^0 & \cdots & x_{n1}^0 \\ x_{12}^0 & x_{22}^0 & \cdots & x_{n2}^0 \\ \vdots & \vdots & & \vdots \\ x_{1p}^0 & x_{2p}^0 & \cdots & x_{np}^0 \end{bmatrix} \begin{bmatrix} y_1^0 \\ \vdots \\ y_n^0 \end{bmatrix} [y_1^0 \cdots y_n^0] \begin{bmatrix} x_{11}^0 & x_{12}^0 & \cdots & x_{1p}^0 \\ x_{21}^0 & x_{22}^0 & \cdots & x_{2p}^0 \\ \vdots & \vdots & & \vdots \\ x_{n1}^0 & x_{n2}^0 & \cdots & x_{np}^0 \end{bmatrix}$$

$$W_1 = \begin{bmatrix} w_{11} & w_{12} & \cdots & w_{1p} \\ w_{21} & w_{22} & \cdots & w_{2p} \\ \vdots & \vdots & & \vdots \\ w_{p1} & w_{p2} & \cdots & w_{pp} \end{bmatrix}$$

$$U_1 = {}^t X^0 X^0 {}^t X^0 Y^0$$

$$U_1 = [y_1^0 \cdots y_n^0] \begin{bmatrix} x_{11}^0 & x_{12}^0 & \cdots & x_{1p}^0 \\ x_{21}^0 & x_{22}^0 & \cdots & x_{2p}^0 \\ \vdots & \vdots & & \vdots \\ x_{n1}^0 & x_{n2}^0 & \cdots & x_{np}^0 \end{bmatrix} \begin{bmatrix} x_{11}^0 & x_{21}^0 & \cdots & x_{n1}^0 \\ x_{12}^0 & x_{22}^0 & \cdots & x_{n2}^0 \\ \vdots & \vdots & & \vdots \\ x_{1p}^0 & x_{2p}^0 & \cdots & x_{np}^0 \end{bmatrix} \begin{bmatrix} y_1^0 \\ \vdots \\ y_n^0 \end{bmatrix}$$

$$U_1 = [U_1]$$

1.3 Calculation of the Regression Coefficients $p_1$ in Step β6 And $q_1$ in Step β7

$$p_1 = \frac{{}^t X^0 T_1}{{}^t T_1 T_1} = ({}^t T_1 T_1)^{-1} \, {}^t X_0 T_1$$

$$p_1 = IV_{1(p \times p)} \begin{bmatrix} x_{11}^0 & x_{12}^0 & \cdots & x_{1p}^0 \\ x_{21}^0 & x_{22}^0 & \cdots & x_{2p}^0 \\ \vdots & \vdots & & \vdots \\ x_{n1}^0 & x_{n2}^0 & \cdots & x_{np}^0 \end{bmatrix} \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix}$$

$$p_1 = \begin{bmatrix} p_{11} & p_{12} & \cdots & p_{1p} \\ p_{21} & p_{22} & \cdots & p_{2p} \\ \vdots & \vdots & & \vdots \\ p_{p1} & p_{p2} & \cdots & p_{pp} \end{bmatrix}$$

$$q_1 =$$

$$\frac{{}^t Y_0 T_1}{{}^t T_1 T_1} = {}^t Y_0 T_1 ({}^t T_1 T_1)^{-1} = [y_1^0 \cdots y_n^0] \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} IV_{1(p \times p)}$$

$$q_1 = [q_1 \cdots q_p]$$

In the preceding, the notation $IV_{1(p \times p)}$ corresponds to the result of the calculation of the reverse matrix of ${}^t T_1 T_1$ in the preceding formula. In involves a square matrix.

1.4 Regression of $X_1$ and $Y_1$ in steps β6 and β7

$$X_1 = X^0 - T_1 {}^t p_1$$

$$X_1 = \begin{bmatrix} x_{11}^0 & x_{12}^0 & \cdots & x_{1p}^0 \\ x_{21}^0 & x_{22}^0 & \cdots & x_{2p}^0 \\ \vdots & \vdots & & \vdots \\ x_{n1}^0 & x_{n2}^0 & \cdots & x_{np}^0 \end{bmatrix} - \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} \begin{bmatrix} p_{11} & p_{12} & \cdots & p_{1p} \\ p_{21} & p_{22} & \cdots & p_{2p} \\ \vdots & \vdots & & \vdots \\ p_{p1} & p_{p2} & \cdots & p_{pp} \end{bmatrix}$$

$$Y_1 = Y^0 - T_1 {}^t q_1$$

-continued $$Y_1 = \begin{bmatrix} y_1^0 \\ \vdots \\ y_n^0 \end{bmatrix} - \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} \begin{bmatrix} q_1 \\ \vdots \\ q_p \end{bmatrix}$$

2 Iteration 2: For, $k=2 \Rightarrow X=X_1$ and $Y=Y_1$ 2.1 Calculation of $T_2$ in step $\beta 3$ and $C_2$ in step $\beta 4$ $$T_2 = X_1 W_2 = \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix} \begin{bmatrix} w_{11} & w_{12} & \cdots & w_{1p} \\ w_{21} & w_{22} & \cdots & w_{2p} \\ \vdots & \vdots & & \vdots \\ w_{p1} & w_{p2} & \cdots & w_{pp} \end{bmatrix}$$

$$T_2 = \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix}$$

$$C_2 = Y_1 U_2 = \begin{bmatrix} y_1 \\ \vdots \\ y_n \end{bmatrix} [U_1] = \begin{bmatrix} c_1 \\ \vdots \\ c_n \end{bmatrix}$$

2.2 Calculation of $W_2$ and $U_2$ in Step $\beta 5$ $$W_2 = {}^t X_1 Y_1 {}^t Y_1 X_1$$

$$W_2 = \begin{bmatrix} x_{11} & x_{21} & \cdots & x_{n1} \\ x_{12} & x_{22} & \cdots & x_{n2} \\ \vdots & \vdots & & \vdots \\ x_{1p} & x_{n2} & \cdots & x_{np} \end{bmatrix} \begin{bmatrix} y_1 \\ \vdots \\ y_n \end{bmatrix} [y_1 \cdots y_n] \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix}$$

$$W_2 = \begin{bmatrix} w_{11} & w_{12} & \cdots & w_{1p} \\ w_{21} & w_{22} & \cdots & w_{2p} \\ \vdots & \vdots & & \vdots \\ w_{p1} & w_{p2} & \cdots & w_{pp} \end{bmatrix}$$

$$U_2 = {}^t Y_1 X_1 {}^t X_1 Y_1$$

$$U_2 = [y_1 \cdots y_n] \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix} \begin{bmatrix} x_{11} & x_{21} & \cdots & x_{n1} \\ x_{12} & x_{22} & \cdots & x_{n2} \\ \vdots & \vdots & & \vdots \\ x_{1p} & x_{n2} & \cdots & x_{np} \end{bmatrix} \begin{bmatrix} y_1 \\ \vdots \\ y_n \end{bmatrix}$$

$$U_2 = [U_2]$$

2.3 Calculation of the Regression Coefficients $p_2$ in Step $\beta 6$ and $q_2$ Step $\beta 7$ $$p_2 = \frac{{}^t X_1 T_2}{{}^t T_2 T_2} = ({}^t T_2 T_2)^{-1} \, {}^t X_1 T_2$$

$$p_2 = IV_{2(p \times p)} \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix} \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix}$$

$$p_2 = \begin{bmatrix} p_{11} & p_{12} & \cdots & p_{1p} \\ p_{21} & p_{22} & \cdots & p_{2p} \\ \vdots & \vdots & & \vdots \\ p_{p1} & p_{p2} & \cdots & p_{pp} \end{bmatrix}$$

$$q_2 = \frac{{}^t Y_0 T_1}{{}^t T_1 T_1} = {}^t Y_0 T_1 ({}^t T_1 T_1)^{-1} = [y_1 \cdots y_n] \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} IV_{1(p \times p)}$$

$$q_2 = [q_1 \cdots q_p]$$

2.4 Regression of $X_2$ and $Y_2$ on $T_2$ in Steps $\beta 6$ and $\beta 7$ $$X_2 = X_1 - T_2 {}^t p_2$$

$$X_2 = \begin{bmatrix} x_{11} & x_{12} & \cdots & x_{1p} \\ x_{21} & x_{22} & \cdots & x_{2p} \\ \vdots & \vdots & & \vdots \\ x_{n1} & x_{n2} & \cdots & x_{np} \end{bmatrix} - \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} \begin{bmatrix} p_{11} & p_{12} & \cdots & p_{1p} \\ p_{21} & p_{22} & \cdots & p_{2p} \\ \vdots & \vdots & & \vdots \\ p_{p1} & p_{p2} & \cdots & p_{pp} \end{bmatrix}$$

$$Y_2 = Y_1 - T_2 {}^t q_2$$

$$Y_2 = \begin{bmatrix} y_1 \\ \vdots \\ y_n \end{bmatrix} - \begin{bmatrix} t_{11} & t_{12} & \cdots & t_{1p} \\ t_{21} & t_{22} & \cdots & t_{2p} \\ \vdots & \vdots & & \vdots \\ t_{n1} & t_{n2} & \cdots & t_{np} \end{bmatrix} \begin{bmatrix} q_1 \\ \vdots \\ q_p \end{bmatrix}$$

The following iterations are deduced from the first two, based on the preceding explanations.

When iteration K has been reached in step $\beta 12$, one obtains, during a synthesis step $\gamma 1$, the following general equation 25, by successively applying equation 23 for k going from 1 to K:

$$Y = Y^0 = T_1 {}^t + T_2 {}^t q_2 + \ldots + T_K {}^t q_K + Y_K = T^t q + Y_K \quad \text{(equation 25)}$$

where the notation $T^t q$ means $\Sigma_1^K T_k {}^t q_k$

By replacing T with its definition from equation 9, or $T = X \cdot W$, one obtains the relationship:

$$Y = Y^0 = X_1 W_1 {}^t q_1 + X_2 W_2 {}^t q_2 + \ldots + X_K W_K {}^t q_K + Y_K = \quad \text{(equation 26)}$$

$$X W^t q + Y_K$$

where the notation $W^t q$ means $\Sigma_1^K W_k {}^t q_k$

By comparison between equations 8 and 26, one obtains, in a second synthesis step $\gamma 2$, the matrix B and the corresponding residue $\varepsilon$, with the relationships:

$$B = W^t q = \Sigma_1^K W_k {}^t q_k \quad \text{(equation 27)}$$

$$\varepsilon = Y_K \quad \text{(equation 28)}$$

Thus, the method of steps $\alpha 1$ to $\alpha 7$ makes it possible to determine a matrix B and a residue $\varepsilon$ that can be used like the matrix $M_{(p \times 1)}$ and the residue R in equation 3, during step c. In other words, the weight values $m_i$ and the residue R of the model are determined during steps $\alpha 1$ to $\alpha 7$.

Steps $\beta 1$ to $\beta 12$, $\gamma 1$ and $\gamma 2$ are in fact sub-steps of step $\alpha 7$.

Setting aside, optionally, the introduction of samples into the reservoir 4, the calculation of the model can be done automatically by the electronic unit 10. In other words, steps α1 to α7 and the sub-steps of step α7 can be automated, like steps a to c.

The invention is described above in the case of its use for a ship propulsion engine. It is, however, applicable to other equipment, for example an auxiliary engine or accessory of a ship, such as a transmission, in particular a marine or wind turbine transmission, or an internal combustion engine of an electrical plant.

Figure 5:
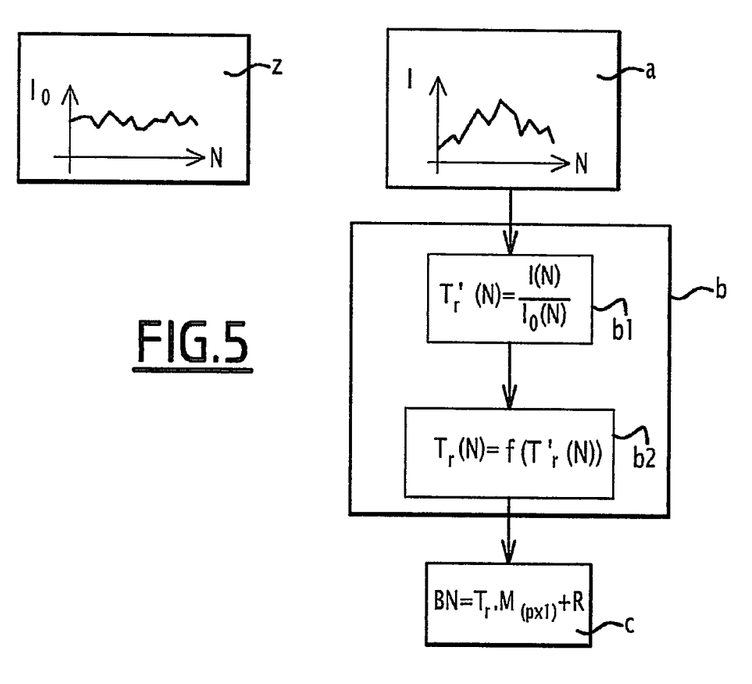
FIG. 5 is a block diagram similar to FIG. 2, for a second method according to the invention.
Figure 6:
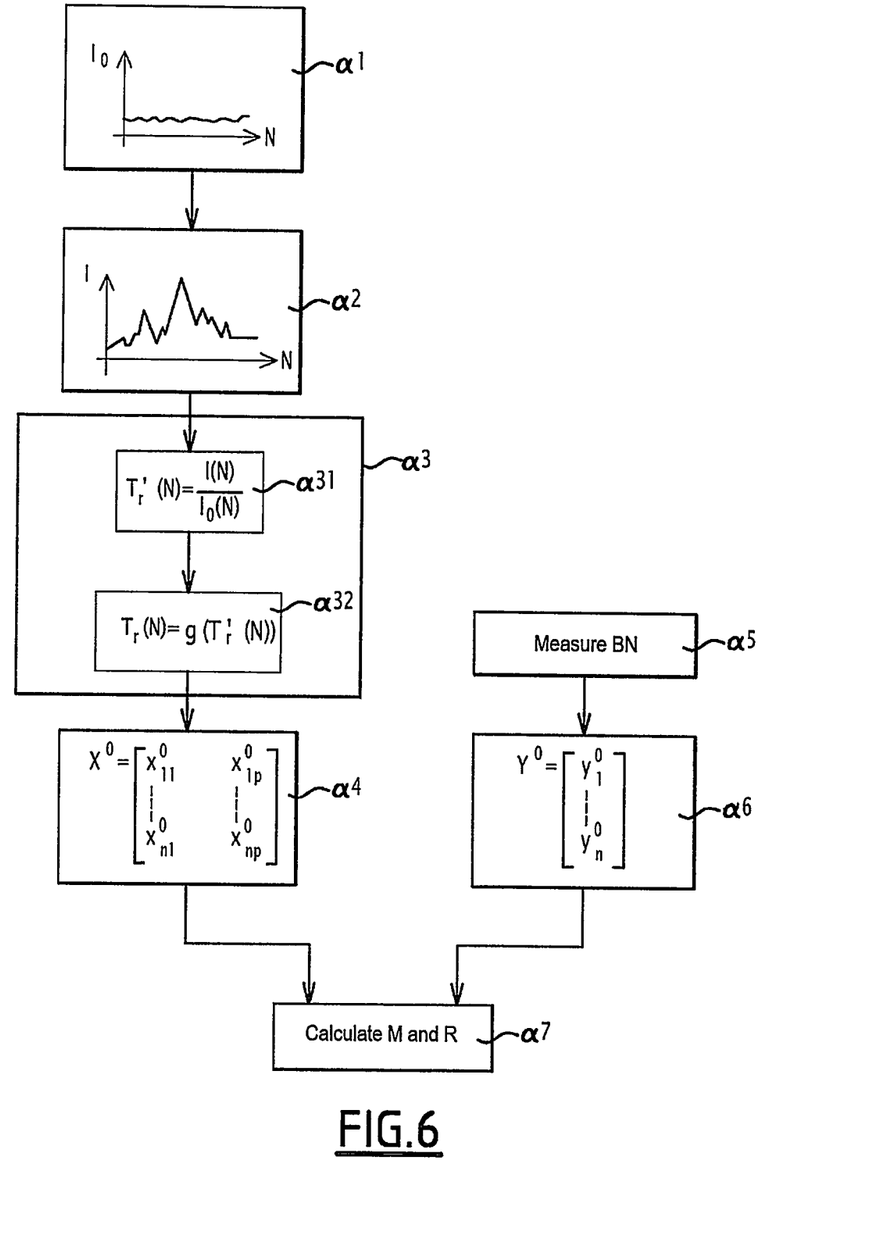
FIG. 6 is a block diagram similar to FIG. 3, for the second method according to the invention.

In the second embodiment shown in FIGS. 5 and 6, the steps similar to those of the first embodiment bear the same references.

Below, we describe only what distinguishes this second embodiment from the previous one.

In this second embodiment, the step b) for calculating the transmittance value $T_r$ comprises two successive elementary steps. A first elementary step b1) consists of calculating, for each wave number N, the ratio T'r(N) of the intensity I(N) of the infrared signal F passing through the sample E to the empty intensity $I_0$(N). This elementary step b1) is comparable to step b) of the first embodiment, but does not lead directly to the determination of the transmittance.

Indeed, step b) of this second embodiment comprises a second elementary step for actual calculation of the transmittance Tr(N) as a corrected value of the ratio T'r(N). The correction consists of expressing the value of the transmittance Tr(N) for a wave number N using a function f whose variable is the ratio T'r(N), in the form $$TN(N)=f(T'r(N)) \quad \text{(equation 29)}$$

The correction done during step b2), by applying the function f, may consist of recalibrating the value of the ratio T'r(N) by removing a baseline, which amounts to declaring the value of the ratio Tr(N) a constant or variable value as a function of the wave numbers. Alternatively or additionally, the correction done during elementary step b2) consists of filtering the value of the ratio T'r(N), or in other words, smoothing.

In this embodiment and as shown in FIG. 6, the prior step α3 is also broken down into two elementary steps, namely a first elementary step α31) comparable to step α31) of the first embodiment and in which a ratio T'r(N) comparable to that mentioned above is calculated, and a second elementary step α32) in which the transmittance value Tr(N) is calculated in the form of a corrected value of this ratio. The correction consists of expressing the value of the transmittance Tr(N) for a wave number N using a function g whose variable is the ratio T'r(N), in the form $$Tr(N)=g(T'r(N)) \quad \text{(equation 30)}$$

The function g is preferably identical to the function f, although this is not mandatory.

The correction of the elementary step α32) may assume the form of filtering and/or the removal of a baseline, as considered above for step b2).

Steps b2) and α32) may be considered pre-processing steps for the raw data T'r(N) to provide the processed data Tr(N).

The invention claimed is:

1. A method for an on-line determination of a basicity index of a liquid body to be characterized by mid-infrared spectroscopy, the method comprising:
   a) detecting an intensity of an infrared signal passing through a sample of the liquid body to be characterized;
   b) subsequent to step a), calculating a transmittance value of infrared waves through the sample for p wave numbers, wherein p is a natural integer greater than or equal to two; and
   c) determining and expressing the basicity index of the liquid body to be characterized in the form of $BN=Tr \cdot M_{(p \times 1)}+R$ where:
      BN is the basicity index of the liquid body to be characterized;
      Tr is a set of transmittance values calculated in step b);
      $M_{(p \times 1)}$ is a set of data of a model, the set of data containing coefficients determined from measured basicity index values and measured transmittance values of reference liquid bodies; and
      R is a residue of the model, determined from the measured basicity index values and the transmittance values of the reference liquid bodies.

2. The method according to claim 1, wherein during step b), the transmittance value for each wave number is calculated as a ratio of the intensity of the infrared signal passing through the sample and a reservoir containing the sample of the liquid body to be characterized to an intensity of an infrared signal passing through the reservoir when empty.

3. The method according to claim 1, wherein step b) comprises:
   b1) calculating, for each wave number, a ratio of an intensity of an infrared signal passing through the sample and a reservoir containing the sample of the liquid body to be characterized to an intensity of the signal passing through the reservoir when empty; and
   b2) calculating the transmittance value in the form of a corrected value of the ratio calculated in step b1).

4. The method according to claim 3, wherein during step b2), the value of the ratio is corrected by filtering and/or by removing a baseline.

5. The method according to claim 1, wherein the transmittance value comprises a unidirectional matrix with one row and p columns and the set of data of a model is a unidirectional matrix with p rows and one column.

6. The method according to claim 1, further comprising the following prior steps carried out to determine the model:
   α1) detecting an intensity of an infrared signal, for the p wave numbers, when in the vacuum;
   α2) detecting an intensity of an infrared signal, for the p wave numbers, within n samples, each representative of a reference liquid body;
   α3) calculating the transmittance of each reference liquid body as a set of values defined, for each wave number, as a ratio of the intensity detected in step α2) to the intensity detected in step α1);
   α4) creating a first set of data of reference, the first set of data of reference comprising the transmittance values calculated in step α3) for the n samples and for the p wave numbers;
   α5) measuring the basicity index of each reference liquid body;
   α6) creating a second set of data of reference, the second set of data of reference comprising the n basicity index values measured in step α5); and
   α7) determining, by calculation, the set of data of the model and the residue of the model, based on the first and second sets data of reference.

7. The method according to claim 6, wherein during step α3), the transmittance of each reference liquid body is calculated as a set of values defined, for each wave number, as a ratio of the intensity detected in step α2) to the intensity detected in step α1).

8. The method according to claim 6, wherein step α3) comprises:
   α3.1) calculating, for each wave number, a ratio of the intensity detected in step α2) to the intensity detected in step α1); and
   α3.2) calculating the transmittance value in the form of a corrected value of the ratio calculated in step α3.1).

9. The method according to claim 6, wherein:
the transmittance value comprises a unidirectional matrix with one row and p columns and the set of data of the model is a unidirectional matrix with p rows and one column;
the first set of data of reference is a two-dimensional matrix with n rows and p columns, each row comprising transmittance values calculated in step α3) for a reference liquid body and p wave numbers and each column comprising transmittance values calculated for a wave number and the n reference liquid bodies; and
the second set of data of reference is a unidirectional matrix with n rows and one column.

10. The method according to claim 6 further comprising the following steps carried out during step α7) to determine the model:
   β1) defining a first set of data of calculation, the first set of data of calculation being an image of the first set of reference data;
   β2) defining a second set of data of calculation, the second set of data of calculation being an image of the second set of reference data;
   β3) defining a first variable dependent on the first set of data of calculation according to the relationship: T=X·W, wherein T is the first variable, X is the first set of calculation data, and W is a first weight coefficient;
   β4) defining a second variable dependent on the second set of data of calculation according to the relationship: C=Y·U, wherein C is the second variable, Y is the second set of calculation data, and U is a second weight coefficient; and
   β5) calculating the values of the two weight coefficients iteratively, while maximizing the covariance of the first and second variables.

11. The method according to claim 10 further comprising the following steps carried out during step α7) to determine the model:
   β6) applying, to each iteration, a linear regression of the first set of data of calculation on the first variable;
   β7) applying, to each iteration, a linear regression of the second set of data of calculation on the first variable;
   β8) calculating, in each iteration, an estimated value of the first set of data of calculation, by applying a transpose of a slope of the linear regression, determined in that iteration, to the first variable calculated in that iteration;
   β9) calculating, in each iteration, an actual value of the first set of data of calculation, by subtracting the estimated value calculated in step β8) from an actual value of this first set of data of calculation calculated in the previous iteration;
   β10) calculating, in each iteration of step β5), an estimated value of the second set of data of calculation, by applying a transpose of a slope of the linear regression, determined in that iteration, to the first calculated variable calculated in that iteration; and
   β11) calculating, in each iteration, an actual value of the second set of data of calculation, by subtracting the estimated value calculated in step β10) from an actual value of this second set of data of calculation calculated in the previous iteration.

12. The method according to claim 11, wherein steps β5) to β11) are repeated until the value of the second set of data becomes lower than a predetermined threshold value.

13. The method according to claim 11, further comprising the following steps to determine the model:
   γ1) expressing the second set of reference data as a function of the first variable according to the relationship:

$$Y^0 = \sum_1^K W_k {}^t q_k + Y_K$$

where:
   K is the number of iterations of step β5), k is a natural number between 1 and K, and $T_k$ is the first variable with iteration rank k,
   ${}^t q_k$ is the transpose of the linear regression slope used in step β10), and
   $Y_K$ is the second set of calculation data with iteration rank K; and
   γ2) determining the set of data of the model and the residue of the model as respectively being equal to:

$$M_{(p \times 1)} = \Sigma_1^K W_k {}^t q_k, \text{ and}$$

$$R = Y_K,$$

where $W_k$ is the weight coefficient with iteration rank k.

14. The method according to claim 10, wherein:
the transmittance value comprises a unidirectional matrix with one row and p columns and the set of data of the model is a unidirectional matrix with p rows and one column;
the first set of data of reference is a two-dimensional matrix with n rows and p columns, each row comprising transmittance values calculated in step α3) for a reference liquid body and p wave numbers and each column comprising transmittance values calculated for a wave number and the n reference liquid bodies;
the second set of data of reference is a unidirectional matrix with n rows and one column;
the first variable is a two-dimensional matrix with n rows and p columns;
the second variable is a unidirectional matrix with n rows and one column;
the first weight coefficient is a two-dimensional matrix with p rows and p columns;
the second weight coefficient is a number;
in each iteration, the weight coefficients are calculated according to the following equations:

$$W_k = {}^t X_{k-1} Y_{k-1} {}^t Y_{k-1} X_{k-1}, \text{ and}$$

$$U_k = {}^t Y_{k-1} X_{k-1} {}^t X_{k-1} Y_{k-1},$$

where an index k applied to a matrix indicates the value of that matrix in iteration k;
the linear regression of step β6) is done based on an equation of the type:

$$X_{k-1} = T_k {}^t p_k + X_k,$$

where $p_k$ is a matrix of regression coefficients determined using the method of least squares and expressed in the form:

$$p_k = \frac{{}^t X_{k-1} T_k}{{}^t T_k T_k};$$

the linear regression of step β7) is done based on an equation of the type:

$$Y_{k-1} = T_k {}^t q_k + Y_{k_2},$$

where $q_k$ is a matrix of regression coefficients determined by the method of least squares and that is expressed in the form:

$$q_k = \frac{{}^t Y_{k-1} T_k}{{}^t T_k T_k}.$$

15. The method according to claim 1, wherein the liquid body is a lubricant circulating in a piece of equipment on a ship.

16. The method according to claim 15, wherein the piece of equipment is an engine.

17. The method according to claim 1, wherein the liquid body is a lubricant.

* * * * *